US008751166B2

(12) United States Patent
Friedlander et al.

(10) Patent No.: US 8,751,166 B2
(45) Date of Patent: Jun. 10, 2014

(54) PARALLELIZATION OF SURPRISAL DATA REDUCTION AND GENOME CONSTRUCTION FROM GENETIC DATA FOR TRANSMISSION, STORAGE, AND ANALYSIS

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/428,339

(22) Filed: Mar. 23, 2012

(65) Prior Publication Data

US 2013/0254218 A1    Sep. 26, 2013

(51) Int. Cl.
*G01N 33/48* (2006.01)
*G06F 19/22* (2011.01)

(52) U.S. Cl.
CPC ..................................... *G06F 19/22* (2013.01)
USPC .......................................................... 702/19

(58) Field of Classification Search
CPC ....................................................... G06F 19/22
USPC .......................................................... 702/19
See application file for complete search history.

(56) References Cited

U.S. PATENT DOCUMENTS

| 7,017,186 | B2 | 3/2006 | Day |
| 2004/0153255 | A1 | 8/2004 | Ahn |
| 2004/0224334 | A1 | 11/2004 | Shibuya |
| 2005/0019787 | A1 | 1/2005 | Berno et al. |
| 2005/0267693 | A1* | 12/2005 | Allard et al. ............... 702/20 |
| 2008/0294692 | A1 | 11/2008 | Angell et al. |
| 2011/0319298 | A1 | 12/2011 | Benner et al. |
| 2012/0230326 | A1 | 9/2012 | Ganeshalingam et al. |

FOREIGN PATENT DOCUMENTS

| CN | 101430742 A | 5/2009 |
| CN | 102081707 A | 6/2011 |
| CN | 102222174 A | 10/2011 |
| JP | 2004240975 | 8/2004 |
| WO | 03081509 A2 | 10/2003 |
| WO | 03083442 A2 | 10/2003 |
| WO | 2005107412 A2 | 11/2005 |
| WO | 2010072382 A1 | 7/2010 |
| WO | 2011076130 A1 | 6/2011 |

OTHER PUBLICATIONS

Craig et al. "Ordering of Cosmid Clones Covering the Herpes Simplex Virus Type I (HSV-I) Genome: A Test Case for Fingerprinting by Hybridisation" Nucleic Acids Research (1990) vol. 18, pp. 2653-2660.*
Grumbach, S. et al.; A New Challenge for Compression Algorithms: Genetic Sequences; Genetic Sequences; 1994;12 pages.
International PCT Search Report for PCT/IB2013/052011; Jun. 18, 2013; 8 pages.
"ssahaSNP: Sequence Search and Alignment by Hashing Algorithm"; http://www.sangerac.uk/resources/software/ssahashp/; Wellcome Trust Sanger Institute; 2011; 2 pages.
He, Q. et al; "A Variable Selection Method for Genome-wide Association Studies"; Dept. of Biostatistics, Univ. of North Carolina; Oct. 2010; pp. 1-8.
"GWASelect: A Variable Selection Method for Genomewide Association Studies"; http://www.bios.unc.edu/~lin/software/GWASelect; at least as early as Feb. 23, 2010; 1 page.
Ruschendorf, F. et al.; "ALOHOMORA: a tool for linkage analysis using 10K SNP Array Data"; BioInformatics Applications Note; vol. 21, No. 9, 2005; pp. 2123-2125.
Hoffmann K. et al.; "easyLINKAGE-Plus—automated linkage analyses using large-scale SNP data"; BioInformatics Applications Note, vol. 21, No. 17 2005. pp. 3565-3567.
International HapMap Project; http://hapmap.ncbi.nlm.nih.gov/cgi-perl/gbrowse/hapmap27_B36/; Feb. 2009; 2 pages.
International HapMap Project: http://en.wikipedia.org/wiki/International_HapMap_Project; Oct. 27, 2002; 4 pages.
Jorde, L. B. et al.; Genetic variation, classification and 'race'; 2004; Nature Genetics 36 (11 Suppl): S28-S33; 8 pages.
Tishkoff, SA et al., Implications of biogeography of human populations for 'race' and medicine; Nature Genetics 36 (11 Suppl): S21-7; 2004; 9 pages.
Brandon, M.G. et al., "Data structures and compression algorithms for genomic sequence data"; BioInformatics—vol. 25: 2009; pp. 1731-1738.
Cao, M.D. et al.: "Agenome alignment algorithm based on compression"; BMC Cioinformatics; 2010; 16 pages.
Christley, S. et al., "Human genomes as email attachments"; Bio Informatics—vol. 25; 2009; pp. 274-275.
Human Genome Diversity Project; http://wikipedia.org/wiki/Human_Genome_Diversity_Project; 2012; 5 pages.
Cavalli-Sforza, L., "The Human Genome Diversity Project: past, present and future";Nature Reviews/Genetics; Apr. 2005; 8 pages.

(Continued)

*Primary Examiner* — Jerry Lin
(74) *Attorney, Agent, or Firm* — Brown & Michaels, PC; John R. Pivnichny

(57) ABSTRACT

A method, computer product, and computer system of reducing an amount of data representing a genetic sequence of an organism, comprising: a computer dividing a reference genome and a sequence of the organism into parts and assigning the parts to one of a plurality of computer processing elements. Within each computer processing element, comparing nucleotides of the genetic sequence of the organism to nucleotides from a part of the reference genome, to find differences where nucleotides of the genetic sequence of the organism which are different from the nucleotides of the reference genome; and storing the surprisal data in a repository. Combining the parts of the surprisal data from the repository to form a complete set of surprisal data representing the differences between the genetic sequence of the organism and the reference genome; and storing the complete set of surprisal data in the repository.

55 Claims, 6 Drawing Sheets

(56) References Cited

OTHER PUBLICATIONS

Rosenberg, N.A.; "Standardized subsets of the HGDP-CEPH Human Genome Diversity Cell Line Panel, accounting for atypical and duplicated samples and pairs of close relatives"; Annals of Human Genetics; Feb. 2006; 40 pages.

Amigo, J. et al.; SPSmart: adapting population based SNP genotype databases for fast and comprehensive web access; BMC Bioinformatics; Oct. 2008; 6 pages.

Li, J.A. et al; "Worldwide Human Relationships Inferred from Genome-Wide Patterns of Variation"; Science—vol. 319; 2008; 6 pages.

Novembre, J. et al., "Genes mirror geography within Europe"; Nature; Nov. 2008; 13 pages.

PCT Search Report for PCT/IB2013/052012 mailed Aug. 15, 2013; 10 pages.

International HapMap Project; http://hapmap.ncbi.nlm.nih.gov/; 2009; 3 pages.

Human Genome Project Information; http://www.oml.gov/sci/techresources/Human_Genome/fag/fags1.shtml; 1990; 9 pages.

Wacker, S.A. et al; Using transcriptome sequencing to identify mechanisms of drug action and resistance; Nature Chemical Biology; Feb. 2012; 37 pages.

\* cited by examiner

Fig. 5

Organism sequence:          ...TAGCAATGA...
                                   ^
                                  485

Reference genome sequence: ...TAGGTTAGA...
                                   ^
                                  485

Surprisal Data:             location of difference: 485
                            number of different nucleic acid bases: 4
                            actual changed nucleic acid bases: CAAT

Fig. 6

Reference genome sequence: ...TAGGTTAGA...
                                   ^
                                  485
                                   +
Surprisal Data:             location of difference: 485
                            number of different nucleic acid bases: 4
                            actual changed nucleic acid bases: CAAT Organism's complete genome: ...TAGCAATGA...
                                   ^
                                  485

US 8,751,166 B2

PARALLELIZATION OF SURPRISAL DATA REDUCTION AND GENOME CONSTRUCTION FROM GENETIC DATA FOR TRANSMISSION, STORAGE, AND ANALYSIS

BACKGROUND

The present invention relates to gene sequencing, and more specifically to parallelization of surprisal data reduction and genome construction from genetic data for transmission, storage and analysis.

DNA gene sequencing of a human, for example, generates about 3 billion ($3 \times 10^9$) nucleotide bases. Currently all 3 billion nucleotide base pairs are transmitted, stored and analyzed. The storage of the data associated with the sequencing is significantly large, requiring at least 3 gigabytes of computer data storage space to store the entire genome which includes only nucleotide sequenced data and no other data or information such as annotations. The movement of the data between institutions, laboratories and research facilities is hindered by the significantly large amount of data and the significant amount of storage necessary to contain the data.

Often time during analysis, a sequence of an organism is compared to a reference genome of the organism. Depending on the number of bases and length of the genome, the comparison can take a significant amount of time, especially when being carried out by only one computer processor.

SUMMARY

According to one embodiment of the present invention a method of reducing an amount of data representing a genetic sequence of an organism using a computer having a plurality of computer processing elements. The method comprising: the computer dividing a reference genome and the genetic sequence of the organism into parts and assigning each of the parts of the reference genome and the parts of the genetic sequence of the organism to one of the plurality of computer processing elements; within each computer processing element, comparing the nucleotides of the assigned part of the genetic sequence of the organism to nucleotides of the assigned part of the reference genome, to find differences where nucleotides of the genetic sequence of the organism are different from the nucleotides of the assigned part of the reference genome, and storing surprisal data in a repository, the surprisal data comprising at least a starting location of the differences within the assigned part of the reference genome, and the nucleotides from the genetic sequence of the organism which are different from the nucleotides of the assigned part of the reference genome, discarding sequences of nucleotides that are the same in the genetic sequence of the organism and the assigned part of the reference genome; the computer retrieving the parts of the surprisal data from the repository; the computer combining the parts of the surprisal data from the repository to form a complete set of surprisal data representing the differences between the genetic sequence of the organism and the reference genome; and the computer storing the complete set of surprisal data in the repository.

According to another embodiment of present invention a method of recreating an entire genome of the organism from a reference genome and surprisal data using a computer having a plurality of computer processing elements, the surprisal data comprising a starting location of the differences within the reference genome, and the nucleotides from the genetic sequence of the organism which are different from the nucleotides of the reference genome, discarding sequences of nucleotides that are the same in the genetic sequence of the organism and the reference genome. The method comprising the steps of: the computer retrieving surprisal data from a repository and dividing the surprisal data into parts; the computer retrieving the reference genome from the repository and dividing the reference genome into parts corresponding to the parts of the surprisal data; the computer assigning parts of the reference genome and corresponding parts of the surprisal data to a plurality of computer processing elements; the computer within each computer processing element, altering the parts of the assigned reference genome based on the corresponding part of the surprisal data by replacing nucleotides at each location in the assigned parts of the reference genome specified by the corresponding parts of surprisal data with the nucleotides from the genetic sequence of the organism in the surprisal data associated with the location and storing the altered parts of the reference genome in the repository; and the computer retrieving the altered parts of the reference genome in the repository combining the altered parts of the reference genome together, resulting in an entire genome of the organism.

According to another embodiment of the present invention, a computer program product for reducing an amount of data representing a genetic sequence of an organism using a computer having a plurality of computer processing elements. The computer program product comprising: one or more computer-readable, tangible storage devices; program instructions, stored on at least one of the one or more storage devices, to divide a reference genome and the genetic sequence of the organism into parts and assign each of the parts of the reference genome and the parts of the genetic sequence of the organism to one of the plurality of computer processing elements; within each computer processing element, program instructions, stored on at least one of the one or more storage devices, to compare the nucleotides of the assigned part of the genetic sequence of the organism to nucleotides of the assigned part of the reference genome, to find differences where nucleotides of the genetic sequence of the organism are different from the nucleotides of the assigned part of the reference genome, and store surprisal data in a repository, the surprisal data comprising at least a starting location of the differences within the assigned part of the reference genome, and the nucleotides from the genetic sequence of the organism which are different from the nucleotides of the assigned part of the reference genome, discarding sequences of nucleotides that are the same in the genetic sequence of the organism and the assigned part of the reference genome; program instructions, stored on at least one of the one or more storage devices, to retrieve the parts of the surprisal data from the repository; program instructions, stored on at least one of the one or more storage devices, to combine the parts of the surprisal data from the repository to form a complete set of surprisal data representing the differences between the genetic sequence of the organism and the reference genome; and program instructions, stored on at least one of the one or more storage devices, to store the complete set of surprisal data in the repository.

According to another embodiment of the present invention, A computer program product for recreating an entire genome of the organism from a reference genome and surprisal data using a computer having a plurality of computer processing elements, the surprisal data comprising a starting location of the differences within the reference genome, and the nucleotides from the genetic sequence of the organism which are different from the nucleotides of the reference genome, discarding sequences of nucleotides that are the same in the genetic sequence of the organism and the reference genome, the computer program product comprising:
one or more computer-readable, tangible storage devices;
program instructions, stored on at least one of the one or more storage devices, to retrieve surprisal data from a repository and dividing the surprisal data into parts;
program instructions, stored on at least one of the one or more storage devices, to retrieve the reference genome from the repository and dividing the reference genome into parts corresponding to the parts of the surprisal data;
program instructions, stored on at least one of the one or more storage devices, to assign parts of the reference genome and corresponding parts of the surprisal data to a plurality of computer processing elements;
within each computer processing element, program instructions, stored on at least one of the one or more storage devices, to alter the parts of the assigned reference genome based on the corresponding part of the surprisal data by replacing nucleotides at each location in the assigned parts of the reference genome specified by the corresponding parts of surprisal data with the nucleotides from the genetic sequence of the organism in the surprisal data associated with the location and store the altered parts of the reference genome in the repository; and program instructions, stored on at least one of the one or more storage devices, to retrieve the altered parts of the reference genome in the repository combining the altered parts of the reference genome together, resulting in an entire genome of the organism According to another embodiment of the present invention, a computer system for reducing an amount of data representing a genetic sequence of an organism, using a computer having a plurality of computer processing elements. The computer system comprising: one or more processors, one or more computer-readable memories and one or more computer-readable, tangible storage devices; program instructions, stored on at least one of the one or more storage devices for execution by at least one of the one or more processors via at least one of the one or more memories, to divide a reference genome and the genetic sequence of the organism into parts and assign each of the parts of the reference genome and the parts of the genetic sequence of the organism to one of the plurality of computer processing elements; within each computer processing element, program instructions, stored on at least one of the one or more storage devices for execution by at least one of the one or more processors via at least one of the one or more memories, to compare the nucleotides of the assigned part of the genetic sequence of the organism to nucleotides of the assigned part of the reference genome, to find differences where nucleotides of the genetic sequence of the organism are different from the nucleotides of the assigned part of the reference genome, and store surprisal data in a repository, the surprisal data comprising at least a starting location of the differences within the assigned part of the reference genome, and the nucleotides from the genetic sequence of the organism which are different from the nucleotides of the assigned part of the reference genome, discarding sequences of nucleotides that are the same in the genetic sequence of the organism and the assigned part of the reference genome; program instructions, stored on at least one of the one or more storage devices for execution by at least one of the one or more processors via at least one of the one or more memories, to retrieve the parts of the surprisal data from the repository; program instructions, stored on at least one of the one or more storage devices for execution by at least one of the one or more processors via at least one of the one or more memories, to combine the parts of the surprisal data from the repository to form a complete set of surprisal data representing the differences between the genetic sequence of the organism and the reference genome; and program instructions, stored on at least one of the one or more storage devices for execution by at least one of the one or more processors via at least one of the one or more memories, to store the complete set of surprisal data in the repository.

According to another embodiment of the present invention, a computer system for recreating an entire genome of the organism from a reference genome and surprisal data using a computer having a plurality of computer processing elements, the surprisal data comprising a starting location of the differences within the reference genome, and the nucleotides from the genetic sequence of the organism which are different from the nucleotides of the reference genome, discarding sequences of nucleotides that are the same in the genetic sequence of the organism and the reference genome. The computer system comprising: one or more processors, one or more computer-readable memories and one or more computer-readable, tangible storage devices; program instructions, stored on at least one of the one or more storage devices for execution by at least one of the one or more processors via at least one of the one or more memories, to retrieve surprisal data from a repository and dividing the surprisal data into parts; program instructions, stored on at least one of the one or more storage devices for execution by at least one of the one or more processors via at least one of the one or more memories, to retrieve the reference genome from the repository and dividing the reference genome into parts corresponding to the parts of the surprisal data; program instructions, stored on at least one of the one or more storage devices for execution by at least one of the one or more processors via at least one of the one or more memories, to assign parts of the reference genome and corresponding parts of the surprisal data to a plurality of computer processing elements; within each computer processing element, program instructions, stored on at least one of the one or more storage devices for execution by at least one of the one or more processors via at least one of the one or more memories, to alter the parts of the assigned reference genome based on the corresponding part of the surprisal data by replacing nucleotides at each location in the assigned parts of the reference genome specified by the corresponding parts of surprisal data with the nucleotides from the genetic sequence of the organism in the surprisal data associated with the location and store the altered parts of the reference genome in the repository; and program instructions, stored on at least one of the one or more storage devices for execution by at least one of the one or more processors via at least one of the one or more memories, to retrieve the altered parts of the reference genome in the repository combining the altered parts of the reference genome together, resulting in an entire genome of the organism.

BRIEF DESCRIPTION OF THE SEVERAL VIEWS OF THE DRAWINGS

FIG. 5 shows a schematic of the comparison of an organism gene sequence to a reference genome sequence to obtain surprisal data.

FIG. 6 shows a schematic of the recreation of an organism genome sequence using a reference genome sequence and surprisal data

DETAILED DESCRIPTION

The illustrative embodiments of the present invention recognize that the difference between the genetic sequence from two humans is about 0.1%, which is one nucleotide difference per 1000 base pairs or approximately 3 million nucleotide differences. The difference may be a single nucleotide polymorphism (SNP) (a DNA sequence variation occurring when a single nucleotide in the genome differs between members of a biological species), or the difference might involve a sequence of several nucleotides. The illustrative embodiments recognize that most SNPs are neutral but some, 3-5% are functional and influence phenotypic differences between species through alleles. Furthermore that approximately 10 to 30 million SNPs exist in the human population of which at least 1% are functional. The illustrative embodiments also recognize that with the small amount of differences present between the genetic sequence from two humans, the "common" or "normally expected" sequences of nucleotides can be compressed out or removed to arrive at "surprisal data"—differences of nucleotides which are "unlikely" or "surprising" relative to the common sequences. The dimensionality of the data reduction that occurs by removing the "common" sequences is $10^3$, such that the number of data items and, more important, the interaction between nucleotides, is also reduced by a factor of approximately $10^3$—that is, to a total number of nucleotides remaining is on the order of $10^3$. The illustrative embodiments also recognize that by identifying what sequences are "common" or provide a "normally expected" value within a genome, and knowing what data is "surprising" or provides an "unexpected value" relative to the normally expected value, the only data needed to recreate the entire genome in a lossless manner is the surprisal data and the genome used to obtain the surprisal data. The illustrative embodiments recognize that by dividing a genome into smaller parts and distributing the smaller parts to different computing elements, such as field programmable gate arrays (FPGA) or complex programmable logic devices (CPLD), allows the identification of what sequences are "common" or provide a "normally expected" value within a genome to be conducted in a significantly less amount of time.

Figure 1:
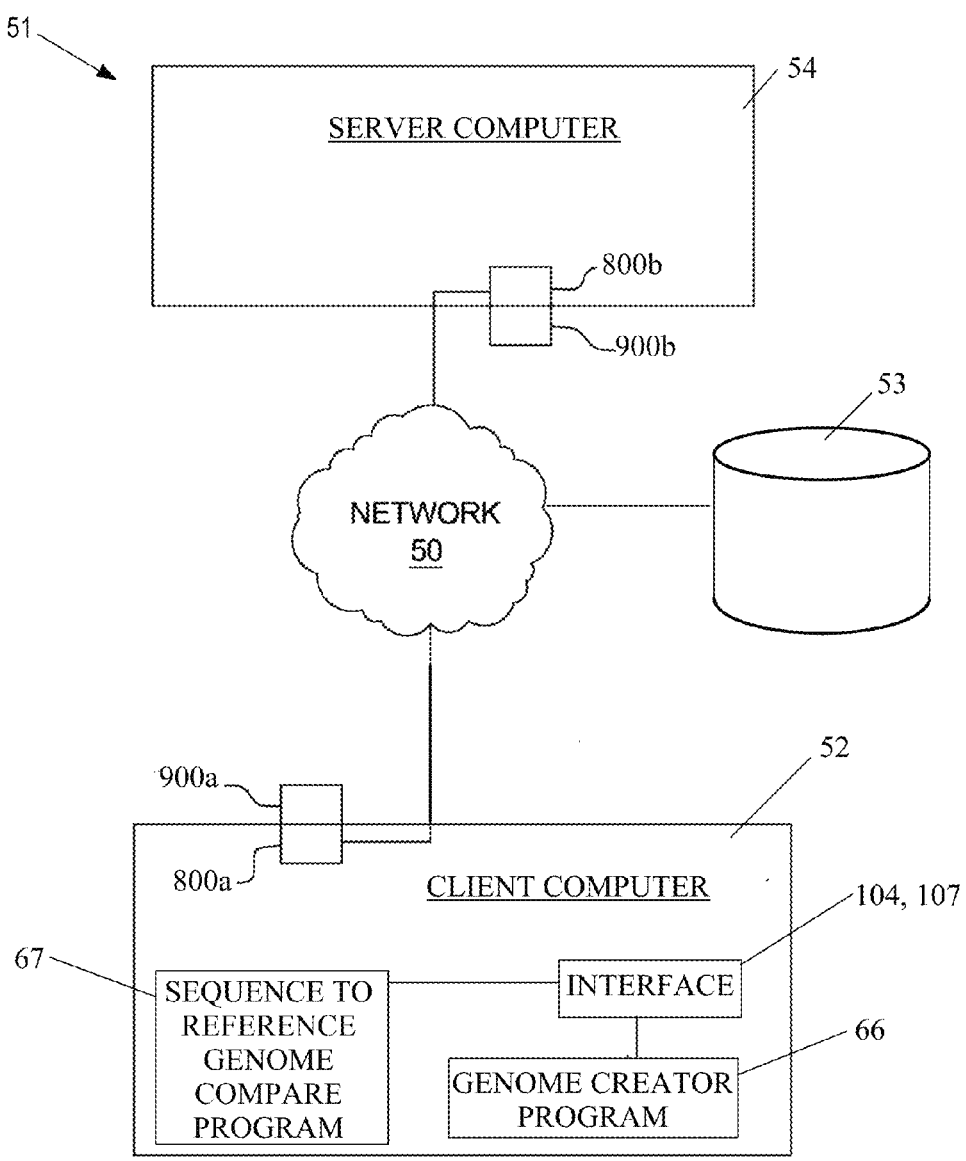
FIG. 1 depicts an exemplary diagram of a possible data processing environment in which illustrative embodiments may be implemented.

FIG. 1 is an exemplary diagram of a possible data processing environment provided in which illustrative embodiments may be implemented. It should be appreciated that FIG. 1 is only exemplary and is not intended to assert or imply any limitation with regard to the environments in which different embodiments may be implemented. Many modifications to the depicted environments may be made.

Referring to FIG. 1, network data processing system 51 is a network of computers in which illustrative embodiments may be implemented. Network data processing system 51 contains network 50, which is the medium used to provide communication links between various devices and computers connected together within network data processing system 51. Network 50 may include connections, such as wire, wireless communication links, or fiber optic cables.

In the depicted example, client computer 52, storage unit 53, and server computer 54 connect to network 50. In other exemplary embodiments, network data processing system 51 may include additional client computers, storage devices, server computers, and other devices not shown. Client computer 52 includes a set of internal components 800*a* and a set of external components 900*a*, further illustrated in FIG. 7. Client computer 52 may be, for example, a mobile device, a cell phone, a personal digital assistant, a netbook, a laptop computer, a tablet computer, a desktop computer, or any other type of computing device.

Client computer 52 may contain an interface 104. Through the interface 104, different reference genomes and surprisal data may be viewed by users. The interface 104 may accept commands and data entry from a user. The interface 104 can be, for example, a command line interface, a graphical user interface (GUI), or a web user interface (WUI) through which a user can access a sequence to reference genome compare program 67 and/or a genome creator program 66 on client computer 52, as shown in FIG. 1, or alternatively on server computer 54. Server computer 54 includes a set of internal components 800*b* and a set of external components 900*b* illustrated in FIG. 7.

In the depicted example, server computer 54 provides information, such as boot files, operating system images, and applications to client computer 52. Server computer 54 can compute the information locally or extract the information from other computers on network 50.

Figure 7:
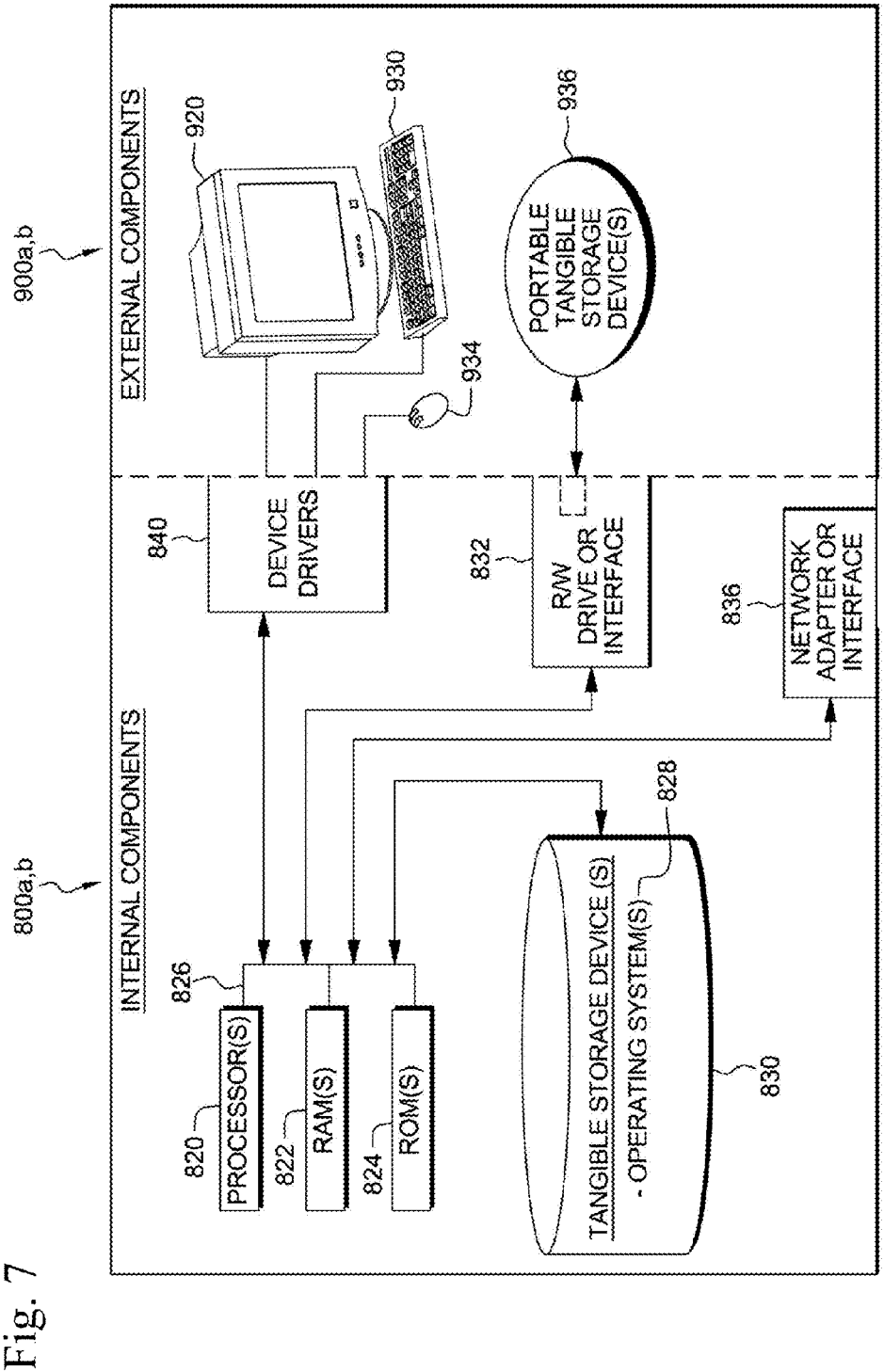
FIG. 7 illustrates internal and external components of a client computer and a server computer in which illustrative embodiments may be implemented.

Program code, reference genomes, and programs such as a sequence to reference genome compare program 67 and/or a genome creator program 66 may be stored on at least one of one or more computer-readable tangible storage devices 830 shown in FIG. 7, on at least one of one or more portable computer-readable tangible storage devices 936 as shown in FIG. 7, on storage unit 53 connected to network 50, or downloaded to a data processing system or other device for use. For example, program code, reference genomes, and programs such as a sequence to reference genome compare program 67 and/or a genome creator program 66 may be stored on at least one of one or more tangible storage devices 830 on server computer 54 and downloaded to client computer 52 over network 50 for use on client computer 52. Alternatively, server computer 54 can be a web server, and the program code, reference genomes, and programs such as a sequence to reference genome compare program 67 and/or a genome creator program 66 may be stored on at least one of the one or more tangible storage devices 830 on server computer 54 and accessed on client computer 52. Sequence to reference genome compare program 67 and/or genome creator program 66 can be accessed on client computer 52 through interface 104. In other exemplary embodiments, the program code, reference genomes, and programs such as sequence to reference genome compare program 67 and genome creator program 66 may be stored on at least one of one or more computer-readable tangible storage devices 830 on client computer 52 or distributed between two or more servers.

Figure 2:
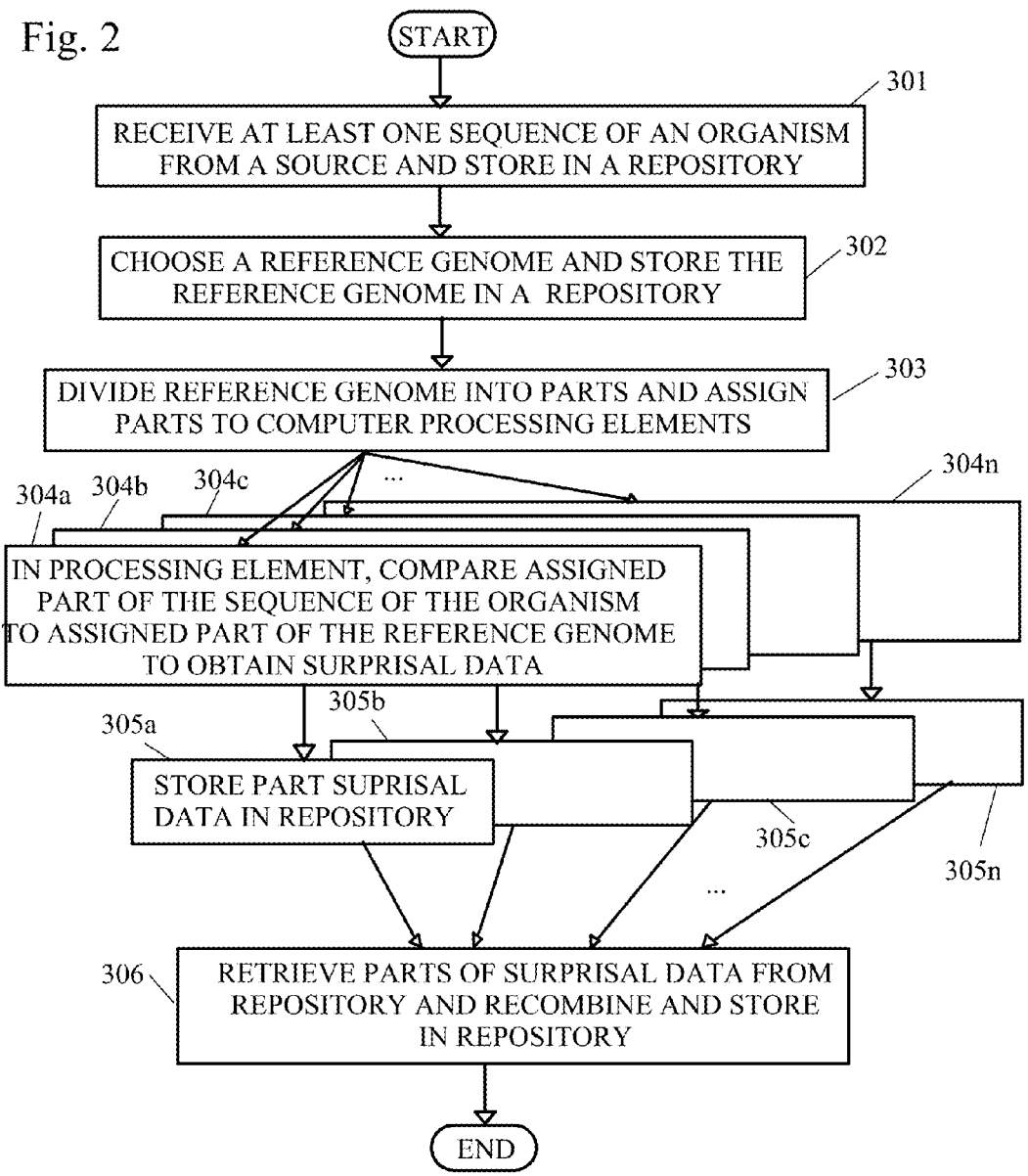
FIG. 2 shows a flowchart of a method of data parallelization of surprisal data reduction of genetic data for transmission, storage, and analysis according to an illustrative embodiment.

FIG. 2 shows a flowchart of a method of parallelization of surprisal data reduction of genetic data for transmission, storage, and analysis according to an illustrative embodiment.

In a first step, the sequence to reference genome compare program 67 receives at least one sequence of an organism from a source and stores the at least one sequence in a repository (step 301). The repository may be repository 53 as shown in FIG. 1. The source may be a sequencing device. The sequence may be a DNA sequence, an RNA sequence, or a nucleotide sequence. The organism may be a fungus, microorganism, human, animal or plant.

Based on the organism from which the at least one sequence is taken, the sequence to reference genome compare program 67 chooses and obtains at least one reference genome and stores the reference genome in a repository (step 302).

A reference genome is a digital nucleic acid sequence database which includes numerous sequences. The sequences of the reference genome do not represent any one specific individual's genome, but serve as a starting point for broad comparisons across a specific species, since the basic set of genes and genomic regulator regions that control the development and maintenance of the biological structure and processes are all essentially the same within a species. In other words, the reference genome is a representative example of a species' set of genes.

The reference genome may be tailored depending on the analysis that may take place after obtaining the surprisal data. For example, the sequence to reference genome compare program 67 can limit the comparison to specific genes of the reference genome, ignoring other genes or more common single nucleotide polymorphisms that may occur in specific populations of a species.

The sequence to reference genome compare program 67 divides the reference genome into parts and assigns at least one part of the reference genome to computer processing elements (step 303). For example, the reference genome may be divided into genes, with at least one gene being assigned to a separate computer processing element, such as a field programmable gate arrays (FPGA) or complex programmable logic devices (CPLD). The computer processing elements may be within the same computer or in separate computers which are connected by a network.

Within each computer processing element, the sequence to reference genome compare program 67 compares the at least one sequence to the part of reference genome to obtain surprisal data (step 304a-304n) and each computer processing element stores only the surprisal data in a repository 53 (step 305a-305n).

The surprisal data is defined as at least one nucleotide difference that provides an "unexpected value" relative to the normally expected value of the reference genome sequence. In other words, the surprisal data contains at least one nucleotide difference present when comparing the sequence to the reference genome sequence. The surprisal data that is actually stored in the repository preferably includes a location of the difference within the reference genome, the number of nucleic acid bases that are different, and the actual changed nucleic acid bases. Storing the number of bases which are different provides a double check of the method by comparing the actual bases to the reference genome bases to confirm that the bases really are different.

The computer processing element controller determines whether the sequence of the organism was compared to all parts of the reference genome and may track the progress of assigned tasks through a time protocol or by when the assigned tasks are complete by the computer processing elements. Once tasks are completed by the computer processing elements, the computer processing element controller may distribute additional tasks to be completed.

The sequence to reference genome compare program 67 retrieves all parts of surprisal data from repository and recombines the parts of the surprisal data and stores the surprisal data in the repository (step 306).

Figure 4:
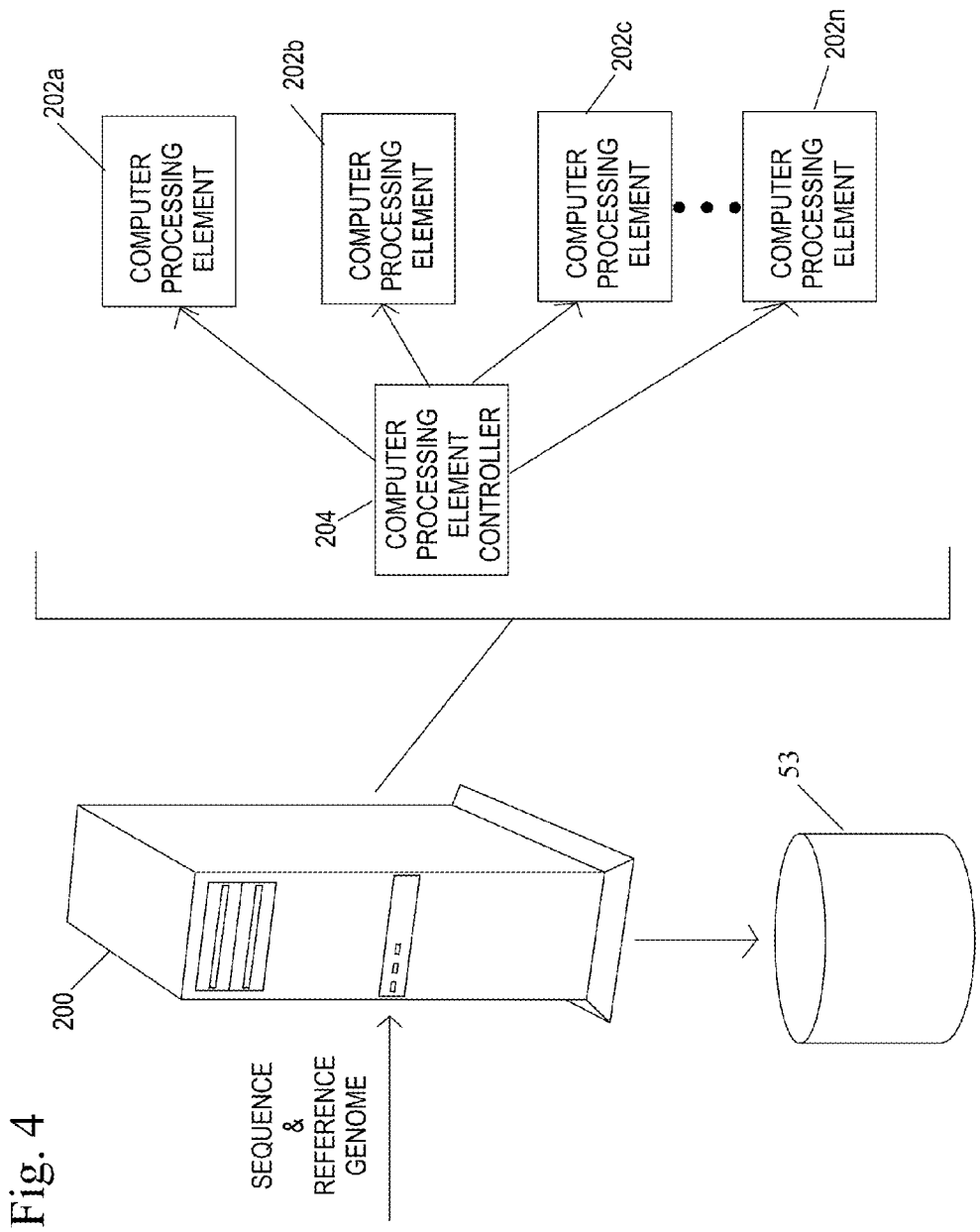
FIG. 4 shows a schematic of a parallelization computer scheme.

Referring to FIG. 4, a computer 200 receives a sequence from an organism and a reference genome. The computer 200 is in communication with a repository, for example repository 53. The computer 200 has numerous computer processing elements 202. A computer processing element controller 204 divides the reference genome into parts, preferably through the sequence to reference genome compare program 67 and assigns at least one part of the reference genome to the computer processing elements 202a-202n. Through the sequence to reference genome compare program 67, the computer processing elements 202a-202n compare the sequence to the parts of the reference genome to obtain surprisal data and stores only the surprisal data in a repository.

The computer processing element controller 204 tracks the progress of assigned tasks through a time protocol or by when the assigned tasks are complete by the computer processing elements 202a-202n. Once tasks are completed by the computer processing elements 202a-202n, the computer processing element controller 204 may distribute additional tasks to be completed.

By assigning genes of the reference genome to separate computer processing elements, the comparison of the at least one sequence to the genes comprising the reference genome to obtain surprisal data is executed in parallel across the separate computer processing elements, significantly decreasing the time necessary to obtain surprisal data.

FIG. 5 shows a schematic of the comparison of an organism sequence to a reference genome sequence to obtain surprisal data. The surprisal data that results from the comparison preferably consists of a location of a difference in the reference genome, the number of bases that were different at the location within the reference genome, and the actual bases that are different than bases in the reference genome at the location. For example, the surprisal data that resulted from comparing the organism sequence to the reference genome shown in FIG. 4 would be surprisal data consisting of: a difference at location 485 of the reference genome; four nucleic acid base differences relative to the reference genome, and the actual bases present in the sequence at the location, for example CAAT (instead of GTTA). The surprisal data and reference genome may be stored on a hard disk.

Figure 3:
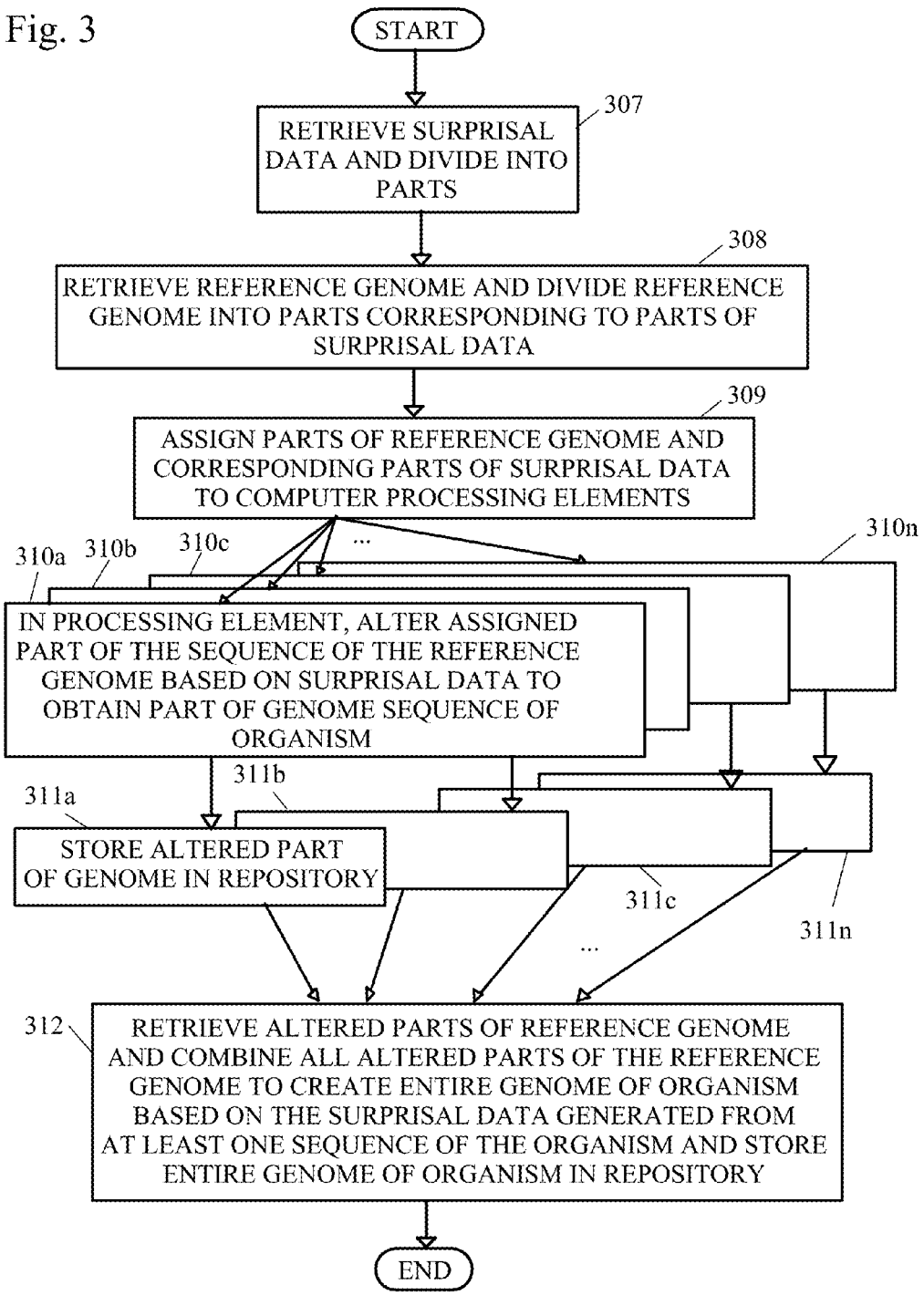
FIG. 3 shows a flowchart of a method of data parallelization to create an entire genome of an organism based on surprisal data.

FIG. 3 shows a flowchart of a method of data parallelization to create an entire genome of an organism based on surprisal data.

The genome creator program retrieves surprisal data and divides the surprisal data into parts (step 307).

The genome creator program retrieves a reference genome and divides the reference genome into parts corresponding to the parts of the surprisal data (step 308). If only the location or index key of the reference genome was retrieved, a genome creator program 66 can obtain the reference genome from a repository.

For example, the reference genome may be divided into genes, with each gene then assigned to a separate computer processing element, such as a field programmable gate arrays (FPGA) or complex programmable logic devices (CPLD) by a computer processing element controller. The computer processing elements may be within the same computer or in separate computers which are connected by a network.

Within each computer processing element, the genome creator program 66 (FIG. 1) finds a location within their part of the reference genome that was indicated as having a difference in the part of surprisal data and alters the bases of the reference genome to be the bases indicated by the part surprisal data to obtain part of the genome sequence of the organism (step 310a-310n). The altered assigned part of the reference genome is stored in a repository 53 (step 311a-311n).

In the example of FIG. 6, based on the surprisal data, a difference is present at location 485, this location is found in the reference genome and GTTA is changed to be CAAT as indicated by the surprisal data.

The computer processing element controller determines whether the reference genome was altered based on the surprisal data and may track the progress of assigned tasks through a time protocol or by when the assigned tasks are complete by the computer processing elements. Once tasks are completed by the computer processing elements, the computer processing element controller may distribute additional tasks to be completed.

Referring to FIG. 3, once the computer processing element controller has determined that all alterations to the reference genome have been made based on the surprisal data (step 310a-310n), the genome creator program 66 (FIG. 1) then retrieves all of the altered parts of the genome and combines all of the altered parts of the reference genome to create an entire genome of an organism based on the surprisal data which was generated from a sequence from the organism (step 312) in a lossless manner.

The surprisal data may be verified by comparing the nucleotides from the genetic sequence of the organism in the surprisal data to the nucleotides in the reference genome at the location. If all of the nucleotides in the surprisal data are different from the nucleotides in the reference genome the surprisal data is verified.

It should be noted that in FIGS. 5 and 6, only a portion of both the organism sequence and the reference genome are shown for clarity, and the sequences shown are chosen randomly and do not represent a real DNA sequence of any sort.

FIG. 7 illustrates internal and external components of client computer 52 and server computer 54 in which illustrative embodiments may be implemented. In FIG. 7, client computer 52 and server computer 54 include respective sets of internal components 800a, 800b, and external components 900a, 900b. Each of the sets of internal components 800a, 800b includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828, sequence to reference genome compare program 67 and genome creator program 66 are stored on one or more of the computer-readable tangible storage devices 830 for execution by one or more of the processors 820 via one or more of the RAMs 822 (which typically include cache memory). In the embodiment illustrated in FIG. 7, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800a, 800b also includes a R/W drive or interface 832 to read from and write to one or more portable computer-readable tangible storage devices 936 such as a CD-ROM, DVD, memory stick, magnetic tape, magnetic disk, optical disk or semiconductor storage device. Sequence to reference genome compare program 67 and genome creator program 66 can be stored on one or more of the portable computer-readable tangible storage devices 936, read via R/W drive or interface 832 and loaded into hard drive 830.

Each set of internal components 800a, 800b also includes a network adapter or interface 836 such as a TCP/IP adapter card. Sequence to reference genome compare program 67 or genome creator program 66 can be downloaded to computer 52 and server computer 54 from an external computer via a network (for example, the Internet, a local area network or other, wide area network) and network adapter or interface 836. From the network adapter or interface 836, sequence to reference genome compare program 67 and genome creator program 66 are loaded into hard drive 830. The network may comprise copper wires, optical fibers, wireless transmission, routers, firewalls, switches, gateway computers and/or edge servers.

Each of the sets of external components 900a, 900b includes a computer display monitor 920, a keyboard 930, and a computer mouse 934. Each of the sets of internal components 800a, 800b also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Sequence to reference genome compare program 67 and genome creator program 66 can be written in various programming languages including low-level, high-level, object-oriented or non object-oriented languages. Alternatively, the functions of a sequence to reference genome compare program 67 and genome creator program 66 can be implemented in whole or in part by computer circuits and other hardware (not shown).

Based on the foregoing, a computer system, method and program product have been disclosed for parallelization of surprisal data reduction of genetic data for transmission, storage, and analysis. However, numerous modifications and substitutions can be made without deviating from the scope of the present invention. Therefore, the present invention has been disclosed by way of example and not limitation.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method of reducing an amount of data representing a genetic sequence of an organism using a computer having a plurality of computer processing elements, the method comprising:

the computer dividing a reference genome and the genetic sequence of the organism into parts and assigning each of the parts of the reference genome and the parts of the genetic sequence of the organism to one of the plurality of computer processing elements;

within each computer processing element, comparing the nucleotides of the assigned part of the genetic sequence of the organism to nucleotides of the assigned part of the reference genome, to find differences where nucleotides of the genetic sequence of the organism are different from the nucleotides of the assigned part of the reference genome, and storing surprisal data in a repository, the surprisal data comprising at least a starting location of the differences within the assigned part of the reference genome, and the nucleotides from the genetic sequence of the organism which are different from the nucleotides of the assigned part of the reference genome, discarding sequences of nucleotides that are the same in the genetic sequence of the organism and the assigned part of the reference genome;

the computer retrieving the parts of the surprisal data from the repository;

the computer combining the parts of the surprisal data from the repository to form a complete set of surprisal data representing the differences between the genetic sequence of the organism and the reference genome;

the computer storing the complete set of surprisal data in the repository;

the computer recreating an entire genome of the organism by:

the computer retrieving the surprisal data from the repository and dividing the surprisal data into parts;

the computer retrieving the reference genome from the repository and dividing the reference genome into parts corresponding to the parts of the surprisal data;

the computer assigning parts of the reference genome and corresponding parts of the surprisal data to each of a plurality of computer processing elements;

each computer processing element altering the parts of the assigned reference genome based on the corresponding part of the surprisal data, by replacing nucleotides at each location in the assigned parts of the reference genome specified by the corresponding parts of surprisal data with the nucleotides from the genetic sequence of the organism in the surprisal data associated with the location, and storing the altered parts of the reference genome in the repository;

the computer retrieving the altered parts of the reference genome from the repository; and the computer combining the altered parts of the reference genome together, resulting in an entire genome of the organism.

2. The method of claim 1, further comprising a computer receiving at least one sequence of an organism from a source and storing the at least one sequence in a repository.

3. The method of claim 1, further comprising a computer obtaining a reference genome corresponding to the organism and storing the reference genome in a repository.

4. The method of claim 1, in which the surprisal data further comprises a number of differences at the location within the reference genome.

5. The method of claim 1, wherein the organism is an animal.

6. The method of claim 5, wherein the organism is human.

7. The method of claim 1, wherein the organism is a microorganism.

8. The method of claim 1, wherein the organism is a plant.

9. The method of claim 1, wherein the organism is a fungus.

10. The method of claim 1, wherein the multiple computer processing elements are field programmable gate arrays.

11. The method of claim 1, wherein the multiple computer processing elements are computer programmable logic devices.

12. The method of claim 1, further comprising a computer processing element controller monitoring completion of the comparison of the nucleotides of the genetic sequence of the organism to the nucleotides of part of the reference genome by each of the computer processing elements.

13. The method of claim 1, further comprising a computer processing element controller monitoring completion of the alteration of the parts of the assigned reference genome by each of the computer processing elements.

14. A computer program product comprising one or more computer-readable, tangible storage devices and computer-readable program instructions which are stored on the one or more storage devices and when executed by one or more processors, implement all the steps of claim 1.

15. A computer system comprising one or more processors, one or more computer-readable memories, one or more computer-readable, tangible storage devices and program instructions which are stored on the one or more storage devices for execution by the one or more processors via the one or more memories and when executed by the one or more processors implement all the steps of claim 1.

16. A method of recreating an entire genome of the organism from a reference genome and surprisal data using a computer having a plurality of computer processing elements, the surprisal data comprising a starting location of the differences within the reference genome, and the nucleotides from the genetic sequence of the organism which are different from the nucleotides of the reference genome, discarding sequences of nucleotides that are the same in the genetic sequence of the organism and the reference genome, the method comprising the steps of:

the computer retrieving surprisal data from a repository and dividing the surprisal data into parts;

the computer retrieving the reference genome from the repository and dividing the reference genome into parts corresponding to the parts of the surprisal data;

the computer assigning parts of the reference genome and corresponding parts of the surprisal data to a plurality of computer processing elements;

the computer within each computer processing element, altering the parts of the assigned reference genome based on the corresponding part of the surprisal data by replacing nucleotides at each location in the assigned parts of the reference genome specified by the corresponding parts of surprisal data with the nucleotides from the genetic sequence of the organism in the surprisal data associated with the location and storing the altered parts of the reference genome in the repository; and the computer retrieving the altered parts of the reference genome in the repository combining the altered parts of the reference genome together, resulting in an entire genome of the organism.

17. The method of claim 16, in which the surprisal data further comprises a number of differences at the location within the reference genome.

18. The method of claim 16, wherein the organism is an animal.

19. The method of claim 18, wherein the organism is human.

20. The method of claim 16, wherein the organism is a microorganism.

21. The method of claim 16, wherein the organism is a plant.

22. The method of claim 16, wherein the organism is a fungus.

23. The method of claim 6, wherein the multiple computer processing elements are field programmable gate arrays.

24. The method of claim 16, wherein the multiple computer processing elements are computer programmable logic devices.

25. The method of claim 16, further comprising a computer processing element controller monitoring completion of the alteration of the parts of the assigned reference genome by each of the computer processing elements.

26. A computer program product for reducing an amount of data representing a genetic sequence of an organism using a computer having a plurality of computer processing elements, the computer program product comprising:

one or more computer-readable, tangible storage devices;

program instructions, stored on at least one of the one or more storage devices, to divide a reference genome and the genetic sequence of the organism into parts and assign each of the parts of the reference genome and the parts of the genetic sequence of the organism to one of the plurality of computer processing elements;

within each computer processing element, program instructions, stored on at least one of the one or more storage devices, to compare the nucleotides of the assigned part of the genetic sequence of the organism to nucleotides of the assigned part of the reference genome, to find differences where nucleotides of the genetic sequence of the organism are different from the nucleotides of the assigned part of the reference genome, and store surprisal data in a repository, the surprisal data comprising at least a starting location of the differences within the assigned part of the reference genome, and the nucleotides from the genetic sequence of the organism which are different from the nucleotides of the assigned part of the reference genome, discarding sequences of nucleotides that are the same in the genetic sequence of the organism and the assigned part of the reference genome;

program instructions, stored on at least one of the one or more storage devices, to retrieve the parts of the surprisal data from the repository;

program instructions, stored on at least one of the one or more storage devices, to combine the parts of the surprisal data from the repository to form a complete set of surprisal data representing the differences between the genetic sequence of the organism and the reference genome;

program instructions, stored on at least one of the one or more storage devices, to store the complete set of surprisal data in the repository;

program instructions, stored on at least one of the one or more storage devices, to recreate an entire genome of the organism by:

retrieving the surprisal data from the repository and dividing the surprisal data into parts;

retrieving the reference genome from the repository and dividing the reference genome into parts corresponding to the parts of the surprisal data;

assigning parts of the reference genome and corresponding parts of the surprisal data to each of a plurality of computer processing elements;

within each computer processing element altering the parts of the assigned reference genome based on the corresponding part of the surprisal data, by replacing nucleotides at each location in the assigned parts of the reference genome specified by the corresponding parts of surprisal data with the nucleotides from the genetic sequence of the organism in the surprisal data associated with the location, and storing the altered parts of the reference genome in the repository;

retrieving the altered parts of the reference genome from the repository; and combining the altered parts of the reference genome together, resulting in an entire genome of the organism.

27. The computer program product of claim 26, wherein the organism is human.

28. The computer program product of claim 26, further comprising program instructions, stored on at least one of the one or more storage devices, to receive at least one sequence of an organism from a source and store the at least one sequence in a repository.

29. The computer program product of claim 26, further comprising program instructions, stored on at least one of the one or more storage devices, to obtain a reference genome corresponding to the organism and store the reference genome in a repository.

30. The computer program product of claim 26, in which the surprisal data further comprises a number of differences at the location within the reference genome.

31. The computer program product of claim 26, wherein the multiple computer processing elements are field programmable gate arrays.

32. The computer program product of claim 26, wherein the multiple computer processing elements are computer programmable logic devices.

33. The computer program product of claim 26, further comprising a computer processing element controller with program instructions, stored on at least one of the one or more storage devices, to monitor completion of the comparison of the nucleotides of the genetic sequence of the organism to the nucleotides of part of the reference genome by each of the computer processing elements.

34. The computer program product of claim 26, further comprising a computer processing element controller with program instructions, stored on at least one of the one or more storage devices, to monitor completion of the alteration of the parts of the assigned reference genome by each of the computer processing elements.

35. A computer program product for recreating an entire genome of the organism from a reference genome and surprisal data using a computer having a plurality of computer processing elements, the surprisal data comprising a starting location of the differences within the reference genome, and the nucleotides from the genetic sequence of the organism which are different from the nucleotides of the reference genome, discarding sequences of nucleotides that are the same in the genetic sequence of the organism and the reference genome, the computer program product comprising:

one or more computer-readable, tangible storage devices;

program instructions, stored on at least one of the one or more storage devices, to retrieve surprisal data from a repository and dividing the surprisal data into parts;

program instructions, stored on at least one of the one or more storage devices, to retrieve the reference genome from the repository and dividing the reference genome into parts corresponding to the parts of the surprisal data;

program instructions, stored on at least one of the one or more storage devices, to assign parts of the reference genome and corresponding parts of the surprisal data to a plurality of computer processing elements;

within each computer processing element, program instructions, stored on at least one of the one or more storage devices, to alter the parts of the assigned reference genome based on the corresponding part of the surprisal data by replacing nucleotides at each location in the assigned parts of the reference genome specified by the corresponding parts of surprisal data with the nucleotides from the genetic sequence of the organism in the surprisal data associated with the location and store the altered parts of the reference genome in the repository; and program instructions, stored on at least one of the one or more storage devices, to retrieve the altered parts of the reference genome in the repository combining the altered parts of the reference genome together, resulting in an entire genome of the organism.

36. The computer program product of claim 35, in which the surprisal data further comprises a number of differences at the location within the reference genome.

37. The computer program product of claim 35, wherein the organism is human.

38. The computer program product of claim 35, wherein the multiple computer processing elements are field programmable gate arrays.

39. The computer program product of claim 35, wherein the multiple computer processing elements are computer programmable logic devices.

40. The computer program product of claim 35, further comprising a computer processing element controller with program instructions, stored on at least one of the one or more storage devices, to monitor completion of the alteration of the parts of the assigned reference genome by each of the computer processing elements.

41. A computer system for reducing an amount of data representing a genetic sequence of an organism, using a computer having a plurality of computer processing elements, the computer system comprising:

one or more processors, one or more computer-readable memories and one or more computer-readable, tangible storage devices;

program instructions, stored on at least one of the one or more storage devices for execution by at least one of the one or more processors via at least one of the one or more memories, to divide a reference genome and the genetic sequence of the organism into parts and assign each of the parts of the reference genome and the parts of the genetic sequence of the organism to one of the plurality of computer processing elements;

within each computer processing element, program instructions, stored on at least one of the one or more storage devices for execution by at least one of the one or more processors via at least one of the one or more memories, to compare the nucleotides of the assigned part of the genetic sequence of the organism to nucleotides of the assigned part of the reference genome, to find differences where nucleotides of the genetic sequence of the organism are different from the nucleotides of the assigned part of the reference genome, and store surprisal data in a repository, the surprisal data comprising at least a starting location of the differences within the assigned part of the reference genome, and the nucleotides from the genetic sequence of the organism which are different from the nucleotides of the assigned part of the reference genome, discarding sequences of nucleotides that are the same in the genetic sequence of the organism and the assigned part of the reference genome;

program instructions, stored on at least one of the one or more storage devices for execution by at least one of the one or more processors via at least one of the one or more memories, to retrieve the parts of the surprisal data from the repository;

program instructions, stored on at least one of the one or more storage devices for execution by at least one of the one or more processors via at least one of the one or more memories, to combine the parts of the surprisal data from the repository to form a complete set of surprisal data representing the differences between the genetic sequence of the organism and the reference genome;

program instructions, stored on at least one of the one or more storage devices for execution by at least one of the one or more processors via at least one of the one or more memories, to store the complete set of surprisal data in the repository;

program instructions, stored on at least one of the one or more storage devices for execution by at least one of the one or more processors via at least one of the one or more memories, to recreate an entire genome of the organism by:

retrieving the surprisal data from the repository and dividing the surprisal data into parts;

retrieving the reference genome from the repository and dividing the reference genome into parts corresponding to the parts of the surprisal data;

assigning parts of the reference genome and corresponding parts of the surprisal data to each of a plurality of computer processing elements;

each computer processing element altering the parts of the assigned reference genome based on the corresponding part of the surprisal data, by replacing nucleotides at each location in the assigned parts of the reference genome specified by the corresponding parts of surprisal data with the nucleotides from the genetic sequence of the organism in the surprisal data associated with the location, and storing the altered parts of the reference genome in the repository;

retrieving the altered parts of the reference genome from the repository; and combining the altered parts of the reference genome together, resulting in an entire genome of the organism.

42. The computer system of claim 41, wherein the organism is human.

43. The computer system of claim 41, further comprising program instructions, stored on at least one of the one or more storage devices for execution by at least one of the one or more processors via at least one of the one or more memories, to receive at least one sequence of an organism from a source and store the at least one sequence in a repository.

44. The computer system of claim 41, further comprising program instructions, stored on at least one of the one or more storage devices for execution by at least one of the one or more processors via at least one of the one or more memories, to obtain a reference genome corresponding to the organism and store the reference genome in a repository.

45. The computer system of claim 41, in which the surprisal data further comprises a number of differences at the location within the reference genome.

46. The computer system of claim 41, wherein the multiple computer processing elements are field programmable gate arrays.

47. The computer system of claim 41, wherein the multiple computer processing elements are computer programmable logic devices.

48. The computer system of claim 41, further comprising a computer processing element controller with program instructions, stored on at least one of the one or more storage devices for execution by at least one of the one or more processors via at least one of the one or more memories, to monitor completion of the comparison of the nucleotides of the genetic sequence of the organism to the nucleotides of part of the reference genome by each of the computer processing elements.

49. The computer system of claim 41, further comprising a computer processing element controller with program instructions, stored on at least one of the one or more storage devices for execution by at least one of the one or more processors via at least one of the one or more memories, to monitor completion of the alteration of the parts of the assigned reference genome by each of the computer processing elements.

50. A computer system for recreating an entire genome of the organism from a reference genome and surprisal data using a computer having a plurality of computer processing elements, the surprisal data comprising a starting location of the differences within the reference genome, and the nucleotides from the genetic sequence of the organism which are different from the nucleotides of the reference genome, discarding sequences of nucleotides that are the same in the genetic sequence of the organism and the reference genome, the computer system comprising:

one or more processors, one or more computer-readable memories and one or more computer-readable, tangible storage devices;

program instructions, stored on at least one of the one or more storage devices for execution by at least one of the one or more processors via at least one of the one or more memories, to retrieve surprisal data from a repository and dividing the surprisal data into parts;

program instructions, stored on at least one of the one or more storage devices for execution by at least one of the one or more processors via at least one of the one or more memories, to retrieve the reference genome from the repository and dividing the reference genome into parts corresponding to the parts of the surprisal data;

program instructions, stored on at least one of the one or more storage devices for execution by at least one of the one or more processors via at least one of the one or more memories, to assign parts of the reference genome and corresponding parts of the surprisal data to a plurality of computer processing elements;

within each computer processing element, program instructions, stored on at least one of the one or more storage devices for execution by at least one of the one or more processors via at least one of the one or more memories, to alter the parts of the assigned reference genome based on the corresponding part of the surprisal data by replacing nucleotides at each location in the assigned parts of the reference genome specified by the corresponding parts of surprisal data with the nucleotides from the genetic sequence of the organism in the surprisal data associated with the location and store the altered parts of the reference genome in the repository; and program instructions, stored on at least one of the one or more storage devices for execution by at least one of the one or more processors via at least one of the one or more memories, to retrieve the altered parts of the reference genome in the repository combining the altered parts of the reference genome together, resulting in an entire genome of the organism.

51. The computer system of claim 50, in which the surprisal data further comprises a number of differences at the location within the reference genome.

52. The computer system of claim 50, wherein the organism is human.

53. The computer system of claim 50, wherein the multiple computer processing elements are field programmable gate arrays.

54. The computer system of claim 50, wherein the multiple computer processing elements are computer programmable logic devices.

55. The computer system of claim 50, further comprising a computer processing element controller with program instructions, stored on at least one of the one or more storage devices, to monitor completion of the alteration of the parts of the assigned reference genome by each of the computer processing elements.

* * * * *